United States Patent
Sachetto et al.

(10) Patent No.: US 7,341,741 B1
(45) Date of Patent: Mar. 11, 2008

(54) PHARMACEUTICAL COMPOSITION FOR THE TREATMENT OF INFLAMMATORY BOWEL DISEASE

(76) Inventors: Jean-Pierre Sachetto, Duchelweiher 13, CH-4144, Arlesheim (CH); William Jeffery Sandborn, 1132-7th St., SW. Rochester, MN (US) 55902; William John Tremaine, 625 Memorial Pkwy., SW. Rochester, MN (US) 55905

( * ) Notice: Subject to any disclaimer, the term of this patent is extended or adjusted under 35 U.S.C. 154(b) by 0 days.

(21) Appl. No.: 09/508,661

(22) PCT Filed: Sep. 25, 1998

(86) PCT No.: PCT/GB98/02899

§ 371 (c)(1),
(2), (4) Date: May 26, 2000

(87) PCT Pub. No.: WO99/16454

PCT Pub. Date: Apr. 8, 1999

(30) Foreign Application Priority Data

Sep. 26, 1997 (GB) .................................. 9720590.0
Nov. 28, 1997 (GB) .................................. 9725346.2

(51) Int. Cl.
*A61F 9/02* (2006.01)
*A61K 9/20* (2006.01)
*A61K 31/175* (2006.01)

(52) U.S. Cl. ................. 424/464; 424/436; 424/195.18; 514/57; 514/782

(58) Field of Classification Search ................ 514/397, 514/400, 966, 57, 782; 424/424, 462, 473, 424/400, 464, 468, 434, 436, 195.18
See application file for complete search history.

(56) References Cited

U.S. PATENT DOCUMENTS

| 5,352,681 A | 10/1994 | Wittebrood et al. |
| 5,380,522 A * | 1/1995 | Day .......................... 424/78.08 |
| 5,972,310 A * | 10/1999 | Sachetto ....................... 424/45 |

FOREIGN PATENT DOCUMENTS

| WO | WO 91/01129 | | 2/1991 |
| WO | WO 92/16214 | | 10/1992 |
| WO | WO 94/04136 | | 3/1994 |
| WO | WO-94/04136 | * | 3/1994 |
| WO | WO 95/16451 | | 5/1995 |
| WO | WO 96/03115 | | 2/1996 |
| WO | WO-96/03115 | * | 2/1996 |
| WO | WO-96/30021 | * | 10/1996 |
| WO | WO 96/30021 | | 10/1996 |
| WO | WO 96/40078 | | 12/1996 |
| WO | WO-98/01112 | * | 1/1998 |
| WO | WO 98/01112 | | 1/1998 |

* cited by examiner

*Primary Examiner*—Johann R. Richter
*Assistant Examiner*—Konata M. George
(74) *Attorney, Agent, or Firm*—Birch, Stewart, Kolasch & Birch, LLP

(57) ABSTRACT

A polysaccharide selected from xanthan gum and HPMC is used for the treatment or prophylaxis of IBD, especially Crohn's Disease, left-sided ulcerative colitis or pouchitis.

20 Claims, No Drawings

PHARMACEUTICAL COMPOSITION FOR THE TREATMENT OF INFLAMMATORY BOWEL DISEASE

This invention relates to use of xanthan gum or hydroxypropylmethylcellulose (HPMC), particularly in the form of enemas for the treatment of inflammatory bowel disease (IBD), and to orally administrable and rectally/vaginally administrable compositions containing xanthan gum or HPMC as a therapeutically active agent.

Xanthan gum (CAS registry no. 1138-66-2) is described in USP NF XVI (p161) as a high molecular weight polysaccharide gum produced by a pure-culture fermentation of a carbohydrate with Xanthomonas campestris. It contains D-glucose and D-mannose as the dominant hexose units, along with D-glucuronic acid and is prepared as the sodium, potassium or calcium salt. It is widely used in pharmaceutical compositions as an emulsifying, stabilising and/or thickening agent.

HPMC (CAS registry no. 9004-65-3), otherwise known as hypromellose, is used as a suspending agent, tablet excipient, demulcent and/or viscosity increasing agent in pharmaceutical compositions. It is been used as a capsule or tablet coating, but the coating is soluble in gastric juices, and so would deliver the active in the capsule in the stomach.

IBD covers chronic non-specific inflammatory conditions of the gastro-intestinal tract, of which the two major forms are Crohn's disease and ulcerative colitis. The aetiology of these diseases is uncertain. Many inflammatory mediators have been proposed including prostanoids, leukotrienes, platelet activating factor, cytokines, and free oxygen radicals. Although specific inhibitors of most of these have been tried in experimental models, the most effective drugs currently available for these diseases have a broad activity against inflammatory processes.

Crohn's disease is characterised by thickened areas of the gastro-intestinal wall, with inflammation extending through all layers, deep ulceration and fissuring of the mucosa, and the presence of granulomas. Affected areas may occur in any part of the gastro-intestinal tract, although the terminal ileum is frequently involved, and they may be interspersed with areas of relatively normal tissue. Fistulas and abscesses may develop. Symptoms depend on the site of disease but may include abdominal pain, diarrhea, fever, weight loss and rectal bleeding.

In ulcerative colitis, disease is continued to the colon and rectum. Inflammation is superficial but continuous over the affected area and granulomas are rare. In mild disease, the rectum alone may be affected (proctitis). In severe disease ulceration is extensive and much of the mucosa may be lost, with an increased risk of toxic dilatation of the colon, a potentially life-threatening complication.

Abdominal colectomy with mucosal protectomy and ileal pouch-anal anastomosis is the preferred treatment for most patients with ulcerative colitis who require surgery. Pouchitis, the most common long-term complication of the procedure, occurs in up to 49% of patients at 10 years. Chronic pouchitis is distinguished from acute pouchitis by duration of symptoms for more than 4 weeks. The aetiology of pouchitis is unknown but it appears that both a history of ulcerative colitis and increased bacterial concentrations (relative to the normal ileum) are factors.

Currently, there is no satisfactory treatment for patients with chronic pouchitis who fail to respond to empiric antibiotic therapy. Although metronidazole is effective in some patients, long-term use is limited by concerns for neurotoxicity with peripheral neuropathy.

Numerous compounds have been examined in the last twenty years to find effective measures for the treatment of IBD. Such compounds include azathioprine, arsenicals, disodium cromoglycate, metronidazole, lignocaine, 5-aminosalicyclic acid (5-ASA), fish oils, thalidomide and cyclosporin. The wide diversity of treatments, is an indication of the complexity and intransigence of IBD.

GB-A-1538123 (published 6 Jan. 1979) disclosed the treatment of diverticulitis with a fibrous cellulosic material and a carboxylic polymer or salt which absorbs water and swells above pH 4. Specified carboxylic polymers include sodium carboxymethylcellulose (sodium CMC).

EP-A-0351987 (published 24 Jan. 1990) disclosed the use of a polyacrylate, preferably a carbomer, for the treatment of IBD by oral or rectal administration.

U.S. Pat. No. 4,917,890 (published 17 Apr. 1990) disclosed the treatment of ulcerative colitis with a mucilaginous polysaccharide aloe extract.

WO-A-94/01436 (published 3 Mar. 1994; corresponding to U.S. Pat. No. 5,380,522) disclosed treatment of irritable bowel syndrome (IBS) with an oral medicament of an anion-binding polymer and a hydrophilic polymer. Exemplified anion-binding polymers include xanthan gum.

WO-A-9407540 (published 14 Apr. 1994; corresponding to EP-A-0620012 & U.S. Pat. No. 5,518,711) disclosed an X-ray contrast medium containing 15-35 w/v % $BaSO_4$ and 0.15-0.6 w/v % xanthan gum dispersed in water. Lower xanthan gum concentrations are used with higher $BaSO_4$ concentrations. The medium is useful for double contrast enema examination of the large and the small intestine to detect inter alia Crohn's disease.

Sandborn et al (Gastroenterology 1994, 106, 1429-1435) reported a placebo-controlled trial of cyclosporin enemas in the treatment of mildly to moderately active left-sided ulcerative colitis. The vehicle for both the test and placebo enemas comprised 60 $cm^3$ water, 5 mg sorbitol (to make the vehicle isomolar) and 500 mg carboxymethylcellulose (CMC) (to suspend the hydrophobic cyclosporin). The placebo enema contained 3.5 $cm^3$ olive oil and use of this enema resulted in clinical improvement in nine out of twenty patients tested.

WO-A-9603115 (published 8 Feb. 1996) disclosed aqueous foamable compositions having a delayed foaming action on expulsion from a pressurised container, comprising a water-immiscible liquefied gas, a water soluble polymer, and optionally, inter alia, a muco-adhesive agent. Exemplified water-soluble polymers include xanthan gum and HPMC and exemplified muco-adhesive agents include CMC. The compositions are of particular use for rectal or vaginal administration of pharmaceuticals to treat inter alia ulcerative colitis or Crohn's disease.

JP-A-08198757 (published 6 Aug. 1996) discloses the use of high amylose starch, preferably administered with food materials, for the treatment of chronic ulcerative colitis.

The present Inventors found that xanthan gum and HPMC are effective per se for the treatment of IBD. This is surprising because, as indicated above, these materials are widely used in pharmaceutical compositions because of their assumed lack of pharmacological activity.

WO 98/01112 (published 15 Jan. 1998; after the claimed priority dates of the present Application) discloses the treatment of distal IBD with a hydrogel formulation consisting essentially of a gelling agent and water with the optional presence of a pH-adjusting agent, plasticizer and/or surfactant. The preferred gelling agents include HPMC and sodium CMC. The only specified distal IBD is ulcerative colitis.

According to a first aspect of the present invention, there is provided the use of a polysaccharide selected from xanthan gum and HPMC as a therapeutically active agent in the manufacture of a medicament for the treatment or prophylaxis of IBD.

By IBD we mean Crohn's Disease and ulcerative colitis including ulcerative proctitis, ulcerative proctosigmoiditis, lymphocytic colitis, intractable distal colitis, ileocolitis, collagenous colitis, microscopic colitis, pouchitis, radiation colitis, and antibiotic-associated colitis. Xanthane gum and HPMC have been found to be particularly useful in the treatment of IBD conditions (such as pouchitis and left-sided ulcerative colitis) normally refractive to conventional therapy.

In a second aspect, the present invention provides a post-gastrically available delayed release oral (DRO) or rectally administrable pharmaceutical composition for the treatment or prophylaxis of IBD, said composition comprising a polysaccharide selected from xanthan gum and HPMC as a therapeutically active agent in an amount effective to treat IBD, together with a pharmaceutically acceptable carrier or vehicle. DRO compositions pass through the stomach substantially unaltered and deliver their active ingredient (which is within the tablet, capsule etc.) typically to the ileum up to and including the colon (i.e. where the diseased mucosa is).

According to a third aspect, the present invention provides a post-gastrically available DRO or rectally administrable pharmaceutical composition for the treatment or prophylaxis of IBD, said composition comprising a polysaccharide selected from xanthan gum and HPMC as the sole therapeutically active agent together with a pharmaceutically acceptable carrier or vehicle.

In a fourth aspect, the present invention provides the use of a polysaccharide selected from xanthan gum and HPMC as the sole therapeutically active agent in the manufacture of a medicament for the treatment or prophylaxis of IBD.

In yet another aspect of the present invention, there is provided a method for the treatment or prophylaxis of IBD comprising contacting the diseased mucosa of the gastrointestinal tract with a therapeutic amount of a polysaccharide selected from xanthan gum and HPMC.

The polysaccharide can be used in the form of pharmaceutically acceptable salts of such as with alkali metals, usually sodium or potassium and alkaline earth metals, usually calcium or barium.

When the polysaccharide is present as the sole active agent, then no other therapeutically active agent such as 5-ASA or a corticosteriod will be present. Optionally, however, other therapeutic agents currently used or proposed for treating IBD can also be used sequentially in a different dosage form or concomitantly in the same dosage form as the polysaccharide. Examples of other such therapeutic agents are 5-ASA; immune modifiers such as azathioprine, cyclosporin and FK506; corticosteroids such as prednisolone, budesonide and hydrocortisone; antibiotics such as metronidazole, ciprofloxacin, amoxicillin, tetracycline and sulphamethoxazole; antidiarreals such as loperamide and codeine sulphate; and local anaesthetic such as lignocaine.

The polysaccharide may be incorporated into a pharmaceutical composition to be administered either rectally, e.g. as an enema, or orally, for example, in coated tablets or capsules as described below. Also, the polysaccharide may be formed into microgranules and coated, for example with Eudragit™ L or S and contained within a capsule similarly coated. In all solid compositions, it is preferable to include a disintegrant. Still further, the polysaccharide may be formulated in a number of dosage forms, e.g. uncoated or coated solid dosage forms for delayed release oral administration, for example using polymers in the Eudragit™ product range.

According to a preferred embodiment of the present invention, the pharmaceutical composition takes the form of an enema formulation such as a liquid or foam enema which is rectally administered to the lower colon. The enema formulations suitably comprise the polysaccharide dissolved or dispersed in a suitable flowable carrier vehicle, such as deionised and/or distilled water. The formulation can be thickened with one or more thickeners, can contain a buffer, and can also comprise an effective amount of a lubricant such as a natural or synthetic fat or oil, e.g. a tris-fatty acid glycerate or lecithin. Non-toxic non-ionic surfactants can also be included as wetting agents and dispersants. Unit doses of enema formulations can be administered from pre-filled bags or syringes. In the case of a pressurised enema formulation the carrier vehicle may also comprise an effective amount of a foaming agent such as n-butane, propane or i-butane, or the foaming agent/propellant could be held separately from the composition such as in a bag-in-bag or bag-in-can system as described in WO-A-9603115 (incorporated herein by reference). Enema foams may also comprise expanding agents and foam-stabilisers.

The viscosity of the enema is preferably 10,000 to 70,000 mPa·s more preferably 10,000 to 70,000 mPa·s and most preferably 10,000 to 40,000 mPa·s. The pH is preferably 3.5 to 7.5, especially 6.5 to 7.5.

A suitable dosage for xanthan gum in an enema or foam enema is 200 to 2000 mg, preferably 250 or 400 to 2000 mg, more preferably 250 to 1650 mg, more preferably still 400 to 1650 mg, especially 550 to 1000 mg, in an aqueous or non-aqueous carrier. The volume of a liquid enema is typically 50 to 200 cm$^3$, preferably about 100 µm$^3$. A suitable % w/w of xanthan gum in an enema is (based on 100 cm$^3$ enema) 0.2% to 2% w/w, more preferably 0.3% to 2% w/w, more preferably still 0.4 to 2% w/w, more preferably still up to 1.65% w/w, and still more preferably 0.55% to 1%. Suitably the volume of a foam enema is 20 to 40 cm$^3$. Based on the above preferred dosages, a suitable % w/w of xanthan gum in a foam enema (based on 40 cm$^3$ foam enema) is 1% to 4.25% w/w, more preferably 1.4% to 2.5%. A buffer is preferably added to the liquid or foam enema of xanthan gum to stabilize the pH. When a buffer is used it increases the viscosity and as a result, the maximum % w/w of xanthan gum that can be incorporated in the enema is about 1.7% w/w.

Typically the viscosity grade of xanthan gum used in a rectally administrable or DRO composition of the invention is 1,200 to 1,600 cP (mPa·s) at 1%.

Typically the viscosity grade of HPMC used in a rectally administrable or DRO composition of the invention is 3 to 100,000 cP (mPa·s). More particularly the grade of HPMC varies depending on the degree of hydroxypropoxy and methoxy substitution. Thus, preferably the degree of methoxy substitution is 15 to 30%, more preferably 19 to 30% such as 19 to 24% and 27 or 28 to 30%. The degree of hydroxypropoxy substitution is preferably 2 to 15%, more preferably 4 to 12%, such as 7 to 12% or 4 to 7.5% The commercially available grades of HPMC include the following:

| Product | % Methoxyl | % Hydroxy-propoxyl | Viscosity cP (Mpa · s) | Relative Rate of Hydration |
|---|---|---|---|---|
| METHOCEL ™ K Premium | 19-24 | 7-12 | 3, 100, 4000, 15000, 100000 | Fastest |
| METHOCEL ™ E Premium | 28-30 | 7-12 | 3, 5, 6, 15, 50, 4000 | Next fastest |
| METHOCEL ™ F Premium | 27-30 | 4-7.5 | 50, 4000 | Slower |

The large range of viscosities allows a high dosage liquid enema or foam enema of HPMC to be formed by using a low viscosity grade of HPMC (i.e. a higher dosage than xanthan gum can be incorporated since the viscosity of the HPMC is less limiting). A suitable dosage of HPMC for a liquid enema or foam enema is 0.2 to 20 g, preferably 1 to 20 g, more preferably 2 to 10 g, still more preferably 5 to 10 g for some IBD disease states and 1 to 5 g for other IBD disease states. A suitable % w/w of HPMC in a liquid enema or foam enema (based on 100 cm$^3$) is 0.2% to 20% w/w, preferably 11 or 2% w/w to 20%, more preferably to an upper limit of 10% w/w, more preferably still 5% to 10%. A suitable % w/w of HPMC in a foam enema (at 40 cm$^3$) is 1% to 50% w/w, more preferably 2.5% to 25% w/w, such as at least 7.5% w/w.

In a further embodiment of the invention, the polysaccharide is administered to the small intestine or colon of a patient by oral ingestion of a post-gastric delayed release (DRO) unit dosage form such as a tablet or capsule, comprising an effective amount of polysaccharide which is enterically coated so as to be released from the unit dosage form in the lower intestinal tract, e.g. in the ileum and/or in the colon of the patient. Enteric coatings remain intact in the stomach, but dissolve and release the contents of the dosage form once it reaches the region where the pH is optimal for dissolution for the coating used.

A DRO formulation can also be achieved by coating a powder or microgranular formulation of the polysaccharide with coatings as mentioned above. The coated microgranules or material may then be compressed into tablets or packed into hard gelatin capsules suitable for oral administration. Suitable coatings and thicknesses to achieve this sustained release are disclosed in EP-A-0572486 (incorporated herein by reference).

The DRO form may optionally also be formulated to give a sustained release of the polysaccharide. The delayed release can be obtained, for example, by complexing the polysaccharide with a polyacrylic acid derivative (a polysaccharide polyacrylate complex) more particularly a polysaccharide carbomer complex. Alternatively particles of the polysaccharide complex could be incorporated into a hydrophobic matrix such as Gelucire™ (Gattefosse, France).

Aqueous film-coating technology is advantageously employed for the enteric coating of pharmaceutical dosage forms. A useful enteric coating is one that remains intact in the low pH of the stomach, but readily dissolves when the optimum dissolution pH of the particular coating is reached. This can vary between pH 3 to 7.5, preferably pH 5 to 7, most preferably pH 5.5 to 6.8, depending on the chemical composition of the enteric coating. The thickness of the coating will depend on the solubility characteristics of the coating material and the site to be treated.

By "delayed release" we mean that release is substantially post-gastrically and by "sustained release" we mean that the total release of the polysaccharide is slow and sustained over a period of time, as opposed to being released as a bolus.

The majority of the release will be targeted to the part of the small intestine or colon where the active disease is prevalent and this varies for Crohn's disease and ulcerative colitis. Thus typically for an enteric coated capsule, the enteric coating should dissolve in the pH of the jejunum (about pH 5.5), ileum (about pH 6) or colon (about pH 6-7) so as to release the majority of the active from the jejunum to the colon—where most of the active disease is located in IBD. More particularly in the case of Crohn's disease most of the active disease is around the terminal ileum and so the enteric coating should dissolve about pH 5.5 to 6. In the case of ulcerative colitis, the disease is mostly in the colon and therefore the enteric coating should dissolve about pH 6 to 7, more particularly about pH 6.8.

Suitably the unit dosage of the polysaccharide in the delayed release oral composition is 200 to 2000 mg, preferably 250 to 2000 mg, more preferably 250 to 1650 mg, more preferably still 400 to 1650 mg, especially 550 to 1000 mg. A suitable % w/w of the polysaccharide in a DRO of the invention is 40 to 90% w/w, more preferably 60 to 80% w/w.

The above also is approximate to the total daily dosage and can be achieved by one or more unit dosages taken once, twice, three or more times daily. For example the total daily dosage is typically 200 to 6000 mg, preferably having a upper dosage limit of about 4000 mg and a lower limit of about 400 mg.

The DRO formulation can be provided as an enteric coated capsule containing the polysaccharide and having a coating thickness and dissolution profile as described in EP-A-0097651 (the contents of which are incorporated herein by reference). Suitable coating include cellulose acetate phthalate, hydroxypropyl methyl cellulose phthalate, ethyl cellulose or polyvinyl acetate phthalate but the preferred coating material is an anionic polymer, especially one having the dissolution profile specified in EP-A-0097651, optionally in admixture with a neutral insoluble but permeable polymer. The presently preferred anionic polymers are anionic carboxylic polymers, i.e. polymers in which the anionic groups are at least predominantly free carboxylic and/or esterified carboxylic groups. It is particularly preferred that the anionic polymers should be acrylic polymers and the presently most preferred polymers are partly methyl esterified methacrylic acid polymers such as poly(methacrylic acid, methyl methacrylate) in which the ratio of free acid groups to ester groups is about 1:1 (e.g. those available from Röhm Pharma GmbH under the Trade Mark EUDRAGIT S). A neutral polymer coating, more specifically poly(ethylacrylate-methylmethacrylate) (e.g. Eudragit™ NE30D) may also be useful in some instances.

Examples of methacrylates (in the Eudragit™ range) for use as enteric coatings in accordance with the invention are as follows.

| Chemical name | Trade name | CAS number |
|---|---|---|
| Poly(methacrylic acid, methyl methacrylate) 1:1 | Eudragit ™ L 100<br>Eudragit ™ L 12.5<br>Euragit ™ L 12.5 P | [25806-15-1] |
| Poly(methacrylic acid, ethyl acrylate) 1:1 | Eudragit ™ L 30 D-55<br>Eudragit ™ L 100-55 | [25212-88-8] |
| Poly(methacrylic acid, methyl methacrylate) 1:2 | Eudragit ™ S 100<br>Eudragit ™ S 12.5<br>Eudragit ™ S 12.5 P | [25086-15-1] |

In general coating thicknesses of about 25 to 200 µm, and especially 75 to 150 µm, are preferred using about 3 to 25 mg, preferably 8 to 15 mg of acidic coating material per $cm^2$ of tablet or capsule surface. The precise coating thickness will however depend upon the solubility characteristics of the acidic material used and site to be treated.

In another preferred DRO or rectally administrable embodiment of the invention, sub 150 µm particles of the polysaccharide or complex thereof (e.g. carbomer complex) is coated (partially or completely) or impregnated with a water insoluble anionic polymer. This prevents the formation of lumps and encourages the resulting hydrophobic particles of polysaccharide to disperse and coat the bowel wall when the contents of the DRO tablet or capsule are released. This technology is described in more detail in International Patent Application no. PCT/GB97/01847 (WO-A-9802573) (incorporated herein by reference).

By "sub 150 µm particles", we mean such that 100% of particles in the DRO will pass through a 150 µm sieve. It is preferred that 100% of the hydrophillic carbomer particles pass a 100 µm sieve screen (i.e. they are sub 100 µm), more preferably at least 90%, especially at least 95%, of the hydrophilic particles pass a 63 µm sieve screen, more preferably a 50 µm sieve screen. The precise particle size must be small enough to provide a composition with a suitable degree of hydrophobicity following coating with the anionic polymer. Preferred particle size may vary according to the nature and amount of the cation present in the complex and the nature and amount of the anionic polymer.

The amount of anionic polymer used will depend upon the nature and amount of the cation present in the salt, the nature of the impregnating anionic polymer, and the degree of hydrophobicity required. A suitable amount can be determined by simple experimentation but usually the anionic polymer will be present in an amount of 10 to 50%, preferably 20 to 40, more preferably 25 to 35 and especially about one third, based on the weight of the carbomer complex. Having regard to the small particle size, the amount of polymer will be less than the theoretical amount required to coat the particles, and the swelling and dissolution of the carbomer will not be controlled by pH.

The polysaccharide particles are impregnated/hydrophobised by milling and passing through a suitable sieve (as aforementioned), stirring the sieved particles into a mixture of e.g. isopropanol and water (solvent) and partly methyl esterified methacrylic acid polymer (e.g. Eudragit™ S100) at from 20 to 40% by weight of the polysaccharide particles (the solvent/coating solution having previously been agitated until clear), stirring and then evaporating the solvent under vacuum at about 50-70° C. to leave coated polysaccharide particles. Thereafter the resulting powder can be filled into gelatin capsules ready for enteric coating.

The invention will now be described by way of the following Examples.

EXAMPLE 1

Enema with HPMC 947.6 g of purified water is preserved with 2 g of methyl and 0.4 g propyl parabens. 50 g (dry basis) of HPMC (Methocel E) low viscosity grade (50 cP/mPa·s) is dissolved under mechanical stirring at room temperature. The solution is degassed (air) under reduced pressure in an oven. A clear viscous enema is obtained having pH 6.9, viscosity (spindle 64, 1.5 rpm-20° C. on Brookfield DV 11): 4,000 mPa·s. The formation is packed in a bag-in-can canister or in an enema plastic pouch or in a PE bottle all having a 100 g enema capacity delivery, thus delivering a full dose of 5,000 mg HPMC.

EXAMPLE 2

Foam Enema Formulation with Xanthan Gum 14,871 g of purified water containing 22 g of dissolved methyl paraben and 2 g of dissolved propyl paraben as preservatives were placed in a 20 liter Moltomat-Universal™ MMU 20 homogenizer. Then 435 g of xanthan gum (Keltrol™ TF) having a water content of 7.6% were dispersed in the preserved water under efficient homogenization and reduced pressure.

30 g of unbleached lecithin were then added and dispersed under homogenization and reduced pressure. At this stage the pH of the viscous gel obtained was 6.3. A solution then made of 0.45 g sodium hydroxide pellets and 20 g of water was added and dispersed under reduced pressure. The pH then was 6.93. Finally 155 g of Polysorbate 80 (non-ionic surfactant) and 4 g of Citral (perfume) were added and dispersed under reduced pressure.

The final foam enema appeared as a slightly hazy gel, having a pH of 7.04 and a viscosity of 40,000 mPa·s at 20° C. as measured using a Brookfield DV II viscometer (1.5 rpm, spindle 63).

A foam enema was then produced using this formulation by adding 2.2 g of n-butane per 100 g of the above formulation in a pressurised mixing unit and the mixture was then filled into bag-in-can aerosol canisters. Each canister contained 23 g of the mixture from which 21 g of foam was delivered through a valve and an applicator, i.e. about 530 mg of xanthan gum per delivered dose.

EXAMPLE 3

Liquid Enema Formulation with Xanthan Gum

To 4,906 g of purified water containing 10 g of dissolved methyl paraben and 2 g of dissolved propyl paraben used as preservatives, 58.95 g of xanthan gum (Keltrol™ TF) containing 6.7% water (i.e. 55 g dry basis) was added in an homogenizer and dispersed under efficient homogenization under reduced pressure. The pH of the gel obtained was 6.05 and the viscosity was 7,500 mPa·s (22° C., 1.5 rpm-spindle 63 Brookfield DV II). At this stage 23 g of sodium citrate. $2H_2O$ was added as buffering agent. The pH went up to 7.15 and the viscosity was 40,000 mPa·s (measured as above). The formulation, which appears as a slightly hazy gel, was then packed into a bag-in-can canister equipped with a valve and an applicator and pressurised with nitrogen. If the bag of the bag-in-can system is filled with 104 g of the formulation above then 100 g of the formulation can be delivered through the valve and applicator corresponding to a dose of 1.1 g of xanthan gum.

EXAMPLE 4

Treatment of Chronic Pouchitis

The enema of Example 2 was given to twenty adult patients who had previously undergone total colectomy with mucosal protectomy and ileal J-pouch anal anastomosis for ulcerative colitis and who had active chronic pouchitis refractory to standard therapy. The patients had chronic pouchitis, as defined as continuous symptoms of pouchitis for more than 4 weeks and a Pouchitis Disease Activity Index (PDAI) score of at least 7 points on an 18 point scale. All patients had either failed or were intolerant to metronidazole as well as other commonly used treatments for pouchitis. Mucosal inflammation, determined by endoscopic examination, was limited to the pouch and did not extend into the ileum proximal to the pouch.

The demographics of the patients entered into the study are presented in Table 1. There were no significant differences in the age, gender distribution, smoking history, time since the diagnosis of ulcerative colitis, duration of pouch function, time since the first episode of pouchitis, duration of the current episode of pouchitis, or in the medications previously used for treatment of pouchitis. All patients had been on medication for pouchitis, previously, and one half of the patients were on concurrent treatment for chronic pouchitis (Table 2).

Three patients had to discontinue treatment because of worsening of symptoms, but none developed dehydration or required hospitalization. Three patients had cramping discomfort in the pouch after taking the enema. One of the patients who developed cramps discontinued treatment because of the discomfort. One patient developed right lower abdominal pain and the study medication was discontinued.

The initial or final endoscopic or histologic scores of the patients are shown in Table 3.

TABLE 1

PATIENT CHARACTERISTICS

| | |
|---|---|
| Number of Patients | 20 |
| Age (mean) | 40 (18-62) |
| Number of Men:Women | 12:8 |
| Number of Cigarette Smokers, current:former:never | 1:2:17 |
| Years since diagnosis of Ulcerative colitis. Median (range) | 9 (3-32) |
| Months of pouch function. Median (range) | 45 (4-161) |
| Months since the first episode of pouchitis. Median (range) | 42 (3-151) |
| Months of current pouchitis episode. Median (range) | 4 (0.8-151) |

TABLE 2

THERAPY FOR POUCHITIS (20 PATIENTS)

| | No. Of Patients | |
|---|---|---|
| Therapy | Current | Previous |
| Antibiotics | | |
| Metronidazole | 3 | 16 |
| Ciprofloxacin | 6 | 15 |
| Amoxicillin/clavulanic acid | 1 | 6 |
| Tetracycline | 0 | 3 |
| Trimethoprine/sulfamethoxazole | 1 | 0 |
| 5-ASA | | |
| Sulfasalazine | 1 | 5 |
| Oral mesalamine | 0 | 5 |
| Mesalamine enemas | 0 | 3 |
| Mesalamine suppositories | 0 | 3 |
| Corticoseroids | | |
| Prednisone | 1 | 7 |
| Hydrocortisone enemas | 0 | 5 |

TABLE 2-continued

THERAPY FOR POUCHITIS (20 PATIENTS)

| | No. Of Patients | |
|---|---|---|
| Therapy | Current | Previous |
| Immune Modifiers | | |
| Azathioprine | 0 | 0 |
| Cylcosporine | 0 | 0 |
| FK506 | 0 | 0 |
| Antidiarrheals | | |
| Loperamide | 5 | 3 |
| Codeine sulfate | 0 | 1 |

DISEASE ACTIVITY AT BASELINE AND COMPLETION OF TREATMENT WITH XANTHAN GUM ENEMA

| | Baseline Median (range) | Completion Median (range) |
|---|---|---|
| Clinical Score | 4 (1, 5) | 3 (0, 4)* |
| Endoscopy Score | 5 (1, 6) | 4 (1, 6) |
| Histology Score | 2 (2, 6) | # 2 (2, 6) |
| Total Score (PDAI) | 11 (7, 16) | 9 (2, 16)* |

*$p < 0.5$ for within-group change. Baseline vs completion (signed rank test with two missing values at completion filled in by overall (groups) Baseline values).

In conclusion, six of the twenty patients discontinued therapy and nine of fourteen patients (64%) who completed the treatment improved (defined as a reduction in the PDAI score of 3 points or more). This is particularly surprising in view of the fact that the patients were refractory to conventional therapy.

The invention claimed is:

1. A method for the treatment of inflammatory bowel disease (IBD) comprising contacting the diseased mucosa of the gastrointestinal tract with a therapeutic amount of a polysaccharide selected from the group consisting of xanthan gum and hydroxypropylmethylcellulose (HPMC) as the sole therapeutic agent.

2. The method according to claim 1, wherein the disease state is pouchitis.

3. The method according to claim 1, wherein the disease state is left sided ulcerative colitis.

4. The method according to claim 1, wherein the disease state is Crohn's disease.

5. The method according to claim 1, wherein the polysaccharide is xanthan gum.

6. The method according to claim 1, wherein the polysaccharide is HPMC.

7. The method according to claim 1, wherein the polysaccharide is administered in the form of an enteric coated dosage form adapted to release its contents within the region of the jejunum in the colon.

8. The method according to claim 1 wherein said therapeutic agent is rectally administered in the form of an rectally administrable pharmaceutical composition.

9. The method according to claim 1, wherein the polysaccharide is administered in the form of a composition comprising a liquid enema containing xanthan gum in a concentration of about 0.4 to about 2% w/w (based on the composition).

10. The method according to claim 1, wherein the said polysaccharide is administered in the form of a composition comprised of a foam enema containing xanthan gum in a concentration of about 1.4 to about 2.5% w/w (based on the composition).

11. The method according to claim 1, wherein said polysaccharide is administered in the form of a composition comprised of a liquid enema containing HPMC in a concentration of about 1 to about 20% w/w (based on the composition).

12. The method according to claim 1, wherein said polysaccharide is administered in the form of a composition comprised of a foam enema containing HPMC in a concentration of about 2.5 to about 25% w/w (based on the composition).

13. The method according to claim 1, wherein said polysaccharide is administered in the form of a composition comprised of a rectally administrable composition comprised of xanthan gum in an amount of about 400 to about 2000 mg per unit dose.

14. The method according to claim 1, wherein said polysaccharide is administered in the form a rectally administrable pharmaceutical composition comprising HPMC in an amount of about 1 to about 20 g per unit dose.

15. A post-gastrically available delayed release oral (DRO) pharmaceutical composition for the treatment or prophylaxis of inflammatory bowel disease (IBD), said composition comprising as the sole therapeutically active ingredient a polysaccharide selected from the group consisting of xanthan gum and hydroxypropylmethylcellulose (HPMC) in an amount effective to treat IBD, together with a pharmaceutically acceptable carrier or vehicle, said composition being an enteric coated dosage form adapted to release its contents within the region of the jejunum to the colon.

16. The DRO pharmaceutical composition according to claim 15, wherein the polysaccharide is xanthan gum.

17. The DRO pharmaceutical composition according to claim 15, wherein the polysaccharide is HPMC.

18. The DRO pharmaceutical composition according to claim 15 in unit dose form containing about 400 to about 2000 mg of the polysaccharide per unit dose.

19. A liquid enema composition for the treatment of inflammatory bowel disease (IBD), said composition comprising hydroxypropylmethylcellulose (HPMC) as the sole therapeutic active agent in an amount effective to treat inflammatory bowel disease, together with a pharmaceutically acceptable carrier or vehicle, said HPMC being present in a concentration of about 1 to about 20% w/w based on the weight of the composition, and in an amount of about 1 to 20 g per unit dose.

20. The liquid enema according to claim 19, wherein the HPMC is in a concentration of about 5 to about 20% w/w/ based on the composition.

* * * * *